United States Patent
Rossby

(10) Patent No.: US 8,380,323 B2
(45) Date of Patent: Feb. 19, 2013

(54) CRANIUM PLUG

(75) Inventor: Christian Rossby, Stockholm (SE)

(73) Assignee: Elekta AB (Publ), Stockholm (SE)

( * ) Notice: Subject to any disclaimer, the term of this patent is extended or adjusted under 35 U.S.C. 154(b) by 544 days.

(21) Appl. No.: 12/424,240

(22) Filed: Apr. 15, 2009

(65) Prior Publication Data

US 2010/0268308 A1    Oct. 21, 2010

(51) Int. Cl.
  *A61B 5/04* (2006.01)
  *A61B 19/00* (2006.01)
  *A61M 5/32* (2006.01)
  *A61F 11/00* (2006.01)
  *A61N 1/00* (2006.01)

(52) U.S. Cl. ........ 607/116; 600/373; 600/377; 600/378; 600/386; 600/393; 600/394; 600/544; 600/545; 604/175; 606/129; 606/130; 606/108; 607/149

(58) Field of Classification Search .................. 600/378, 600/373, 377, 386, 393, 394, 544, 545; 604/17, 604/48, 175, 523, 524, 174; 606/108, 129, 606/130; 607/115, 116, 126, 139
See application file for complete search history.

(56) References Cited

U.S. PATENT DOCUMENTS

| 4,328,813 | A | 5/1982 | Ray |
| 5,464,446 | A | 11/1995 | Dreessen et al. |
| 6,324,433 | B1 | 11/2001 | Errico |
| 6,356,792 | B1 * | 3/2002 | Errico et al. ................ 607/116 |
| 7,004,948 | B1 * | 2/2006 | Pianca et al. ................ 606/129 |
| 2005/0015128 | A1 | 1/2005 | Rezai et al. |
| 2005/0182423 | A1 * | 8/2005 | Schulte et al. ................ 606/130 |
| 2005/0182425 | A1 | 8/2005 | Schulte et al. |
| 2007/0233158 | A1 | 10/2007 | Rodriguez |
| 2009/0112327 | A1 | 4/2009 | Lane et al. |

FOREIGN PATENT DOCUMENTS

WO    WO 2008/119041 A1    10/2008

* cited by examiner

*Primary Examiner* — Niketa Patel
*Assistant Examiner* — Lindsey G Hankins
(74) *Attorney, Agent, or Firm* — Birch, Stewart, Kolasch & Birch, LLP

(57) ABSTRACT

The present invention relates to a device for securing medical leads in a cranial burr hole, in particular, for securing a brain stimulation lead within such a burr hole. The device includes a circular socket element adapted to be secured within a burr hole of the skull of a patient, the circular socket element having a through lead passage arranged to have the lead pass therethrough, the lead passage including passage walls including at least one resilient partition wall extending from an inner wall of the circular socket element, and the circular socket element having at least one inner compartment delimited by the partition wall. Further, the device includes a cap element having a circular upper portion being arranged to mate with the socket element, the circular upper portion having at least one protruding member arranged to co-operate with the at least one inner compartment when placed into the compartment so as to apply a radial pressure on the at least one resilient partition wall such that a lead passing through the passage is fixated in the passage by a resulting radial pressing force.

21 Claims, 2 Drawing Sheets

CRANIUM PLUG

FIELD OF THE INVENTION

The present invention relates to a device for securing medical leads in a cranial burr hole, in particular, for securing a brain stimulation lead within such a burr hole.

BACKGROUND OF THE INVENTION

Electrical stimulation of the brain is an increasingly important approach for treatment of disorders such as Parkinson's disease, essential tremor and dystonia, and for relief of chronic pain. This method can also be used to treat a wide array of neuropsychiatric problems, such as depression, epilepsy, obsessive compulsive disorder or obesity. In general, such stimulation devices interact with the brain by delivering current through an implanted probe in order to modulate brain activity. A typical electrical brain stimulation system comprises a pulse generator operatively connected to the probe via an electrical lead at the distal end. Further, the lead has a connector assembly at the proximal end designed to connect to the pulse generator. Electrical signals are transmitted through the lead to the probe or electrode and thus the desired site in the patient's brain. Normally, access to the desired site in the brain is accomplished by drilling a hole in the patient's skull or cranium using a cranial drill, also called a burr.

As a part of the implant procedure, the probe or electrode must be stabilized in the brain. However, direct attachment of electrical and chemical probes to the brain tissue is impractical. A more easily implementable solution is a system of flexible probes that bend and float with the brain as the brain moves within the cranial cavity. Such probes are secured to the cranium. In this manner, mechanical forces from the outside of the cranium are prevented from acting on the brain-to-probe interface.

In a typical surgical procedure to implant a neurostimulation system for DBS ("Deep Brain Stimulation"), the surgical procedure begins with placing a stereotactic headframe around the patient's head to keep the head stationary. The stereotactic frame also helps the surgeon in the placement of the lead used for the stimulation. Thereafter, the surgeon obtains images of the brain using imaging equipment such as computed tomography (CT) or magnetic resonance imaging (MRI) to map the brain and localize a target site within the brain. In order to provide access to the brain, the surgeon drills a burr hole into the patient's skull. Then, the surgeon inserts a temporary recording stimulation lead into the target site of the brain to test the stimulation, for example, to maximize symptom suppression and minimize side effects before placement of a permanent stimulation electrode lead. When the exact target site of the brain has been determined by the surgeon, the temporary stimulation lead is removed and the surgeon commences the process of inserting the permanent stimulation electrode lead. Using the stereotactic frame and a drive unit, the stimulation electrode lead is inserted through the burr hole in the patient's skull and implanted in the target site within the brain. Once the lead is positioned and tested to determine that the results of stimulation are satisfactory, it is critical that it is not moved. A movement as little as one millimeter of electrode displacement may cause unsatisfactory results or even injury to the brain. Traction on the portion of the lead positioned outside the cranium may cause movement on the portion of the lead positioned within the brain. As understood, it is crucial to achieve a firm and reliable anchoring of the lead in the burr hole. Accordingly, great efforts have been made to obtain reliable means for securing a lead within the burr hole.

For example, in U.S. Pat. No. 4,328,813 a system for anchoring a brain lead within a cranial burr hole is disclosed. The system includes an annular socket having a lead passage and being designed to engage with the burr hole. A plug is arranged to cooperate with the socket and lead passage to secure the lead within the passage and between the plug and socket. However, engagement of the socket and plug according to U.S. Pat. No. 4,328,813 may cause dislodgement of the lead or may pull the lead, which as mentioned above can cause serious problems.

Furthermore, in U.S. Pat. No. 5,464,446 a lead anchoring system is disclosed. The lead anchoring system includes a plug having a central passage, a cap configured to fit the over the plug to seal the burr hole and fixate the lead. A groove is provided in the plug to allow for a suture to be wrapped around the plug to secure the lead in a lead passage of the plug. Thus, the procedure of securing the lead by winding the suture in the groove and attaching the suture may be cumbersome for the surgeon.

In U.S. Pat. No. 5,865,842 a connector system for anchoring a lead or catheter in a cranial burr hole is disclosed. The system includes a base plate, with an adaptor for adapting to a burr hole size, and two element fixation subassembly positioned within the base plate for enabling fixation of the lead to the plate after positioning of the lead with the stereotactic instrument. The fixation subassembly includes a compression seal of compressible material and a compression screw. This construction is mechanically complicated, which may render it expensive to manufacture. Further, it requires a wrench or tool to screw the compression screw into proper position.

A further approach is presented in WO 2008/119041 where an apparatus for securing an implantable lead within tissue, for example, the brain of a patient by fixating the apparatus to the skull of the patient using screws. In particular, the apparatus includes a base adapted to be secured to the patient's skull adjacent a craniotomy using screws, which are screwed into the skull of the patient. This approach thus requires further incisions and holes in the tissue and skull in addition to the burr hole for the implanted stimulation lead.

Hence, there is a need within the art for an improved system and device for firmly securing a medical lead, such as a stimulation lead, in burr hole in a reliable manner. Further, it is important that the lead can be firmly secured without risking any damage on the lead during the securing procedure or during its use.

SUMMARY OF THE INVENTION

Thus, an object of the present invention is to provide an improved system and device for firmly securing a medical lead, e.g. a stimulation lead for delivering electrical stimulation pulses to the brain from a neurogenerator for deep brain stimulation, within a burr hole in a reliable manner.

A further object of the present invention is to provide an improved system and device for firmly securing a medical lead, e.g. a stimulation lead for delivering electrical stimulation pulses to the brain from a neurogenerator for deep brain stimulation, within a burr hole without risking any damage on the lead.

Another object of the present invention is to provide an improved system and device for firmly securing a medical lead, e.g. a stimulation lead for delivering electrical stimulation pulses to the brain from a neurogenerator for deep brain stimulation, within a burr hole in a reliable manner that is easy and cheap to manufacture.

These and other objects are achieved by the present invention as defined by the independent claims. A selection of possible embodiments is defined by the dependent claims. However, as the skilled person will be aware of when studying the specification following hereinafter, there are a number of further and/or alternative embodiments of the present invention that are conceivable.

According to an aspect of the present invention, there is provided a device for securing a medical lead within cranial hole in connection with craniotomy. For example, a stimulation lead for delivering electrical stimulation pulses to the brain from a neurogenerator for deep brain stimulation. The device includes a circular socket element adapted to be secured within a burr hole of the skull of a patient, the circular socket element having a through lead passage arranged to have the lead pass therethrough, the lead passage including passage walls including at least one resilient partition wall extending from an inner wall of the circular socket element, and the circular socket element having at least one inner compartment delimited by the partition wall. Further, the device includes a cap element having a circular upper portion being arranged to mate with the socket element, the circular upper portion having at least one protruding member arranged to co-operate with the at least one inner compartment when placed into the compartment so as to apply a radial pressure on the at least one resilient partition wall such that a lead passing through the passage is fixated in the passage by a resulting radial pressing force.

Thus, the present invention is based on the idea of providing a socket element to be fitted in the burr hole in the skull of the patient with means for locking the stimulation lead by an applied pressure force such that the lead is firmly secured in a through lead passage of the socket without applying traction forces on the lead which may dislodge the lead and thus, in turn, the electrodes. The means for locking includes a resilient wall which co-operates with a protruding member of a cap arranged to be placed in engagement with the socket to seal the socket and protect the brain, and to secure the lead within the socket and the socket within the burr hole. To elaborate, the resilient wall co-operates with the protruding member in that the protruding member, when pushed into the socket element, presses the resilient inner partition wall of the socket against the lead in a radial direction and against an opposite wall of the lead passage, thereby firmly securing the lead in the lead passage. The protruding element of the cap is also arranged to co-operate with an outer wall of the socket such that the socket element is secured in the burr hole by means of an expansion force. By this design, it is possible to secure the lead in a firm and reliable way without applying traction force or pressure force in a longitudinal direction, i.e. a direction along the extension of the lead, which may dislodge the lead during the implantation procedure. The fact that the resilient partition wall acts as an intermediary force transferring element or buffer between the protruding element applying the pressure and the lead also entails that damage on the lead can be avoided. Furthermore, the present invention also achieves a secure and reliable fixation of the lead over time.

According to an embodiment of the present invention, the at least one protruding member is arranged to engage with a slot arranged in the outer wall of the socket element such that the socket element is secured in the burr hole by an expansion force. Thereby, a further improved fixation of the socket element within the burr hole is achieved due to the slight expansion of the socket element that is obtained when the protruding member enters into the slot and thereby expands an outer diameter of the socket element.

In an embodiment of the present invention, the lead passage is delimited by a non-resilient longitudinal passage wall and the resilient partition wall, wherein the lead, in a fixated state, is fixated between the resilient passage wall and the passage wall by means of the radial pressure force applied by the protruding member.

According to an embodiment of the present invention, an upper surface of the circular socket element, facing the cap element when placed in the socket element, is arranged with at least one groove from an outer periphery of the socket element to the lead passage, wherein the lead can be fitted or accommodated into the groove.

In an embodiment of the present invention, the partition wall includes pressure enhancing means arranged to co-operate with the protruding element so as to enhance the radial pressure. According to an alternative, the pressure enhancing means is an inclined shoulder arranged on a side of the partition wall facing the inner compartment, the shoulder being arranged to co-operate with the protruding element so as to enhance the radial pressure.

In a further embodiment of the present invention, the circular plate of the cap element is arranged to be foldable. For example, the circular upper portion of the cap element may be provided with hinge means that entails that the cap element can be inserted into the socket element before the lead has been finally positioned. When the lead has been positioned, the foldable part of the cap element is folded down and the socket element is sealed and secured into the burr hole and the lead is secured in the lead passage. In one embodiment, the foldable part is provided with the protruding member.

The securing device according to the present invention may be employed with a stimulation lead, a sensing lead, a combination thereof or any other elongated member requiring passage through the cranium. Further, it should be noted, the securing device according to the present invention also may be employed with more than one stimulation lead, for example, with two stimulation leads.

BRIEF DESCRIPTION OF THE DRAWINGS

Preferred embodiments of the invention will now be described in greater detail with reference to the accompanying drawings, in which.

DETAILED DESCRIPTION OF EMBODIMENTS OF THE INVENTION

Figure 1:
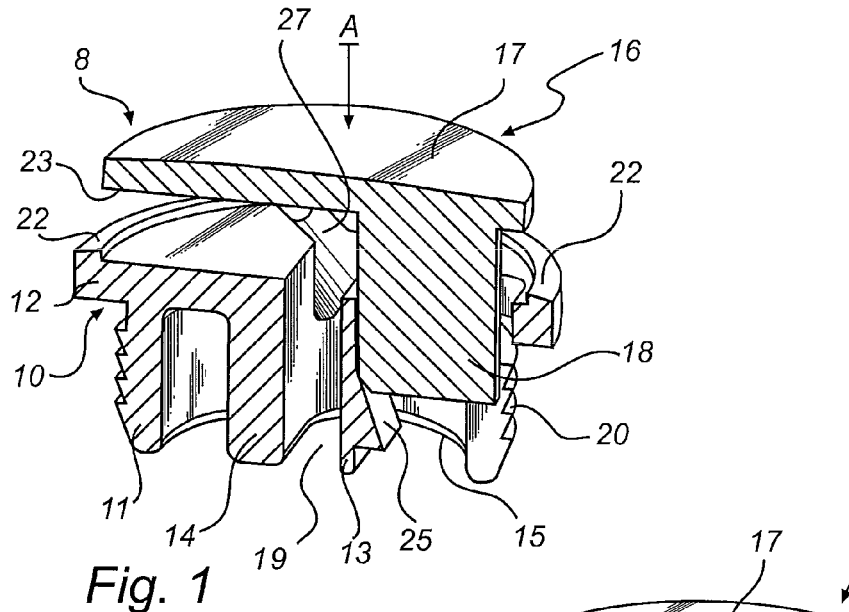
FIG. 1 is an exploded view of an embodiment of the present invention in cross section.

In the description that follows, like parts are indicated throughout the specification and drawings with the same reference numerals, respectively. The figures are schematically and not drawn to scale and the proportions of certain parts may be exaggerated for convenience of illustration.

The present invention provides a device and system for securing a lead within in cranial burr hole, for example, in connection with deep brain stimulation (DBS) that is reliable and easy and cheap to manufacture. In the context of this application, the term "lead" is used herein in its broadest sense and may include a stimulation lead, a sensing lead, and any combination of these leads or any other elongated member such as a catheter. For the purpose of this application, the terms "upper" and "lower" relate to the orientation of the device for securing a lead in relation to the cranium. For example, a surface of the cap element facing outwards in relation to the socket element when secured within a burr hole is an upper (or outer) surface whereas a surface of the cap element facing the socket element is a lower (or inner) surface.

The lead connects a pulse generator operatively to the brain, within a hole through the cranium of skull. The lead has at least one electrode located at its distal end, designed to be implanted within the patient's brain, and a connector assembly at its proximal end, designed to be connected to an internal, i.e. an implanted, pulse generator or an external pulse generator. Electrical signals can be transmitted through the lead to the electrodes from the pulse generator and thus to the desired site of the patient's brain.

Figure 2:
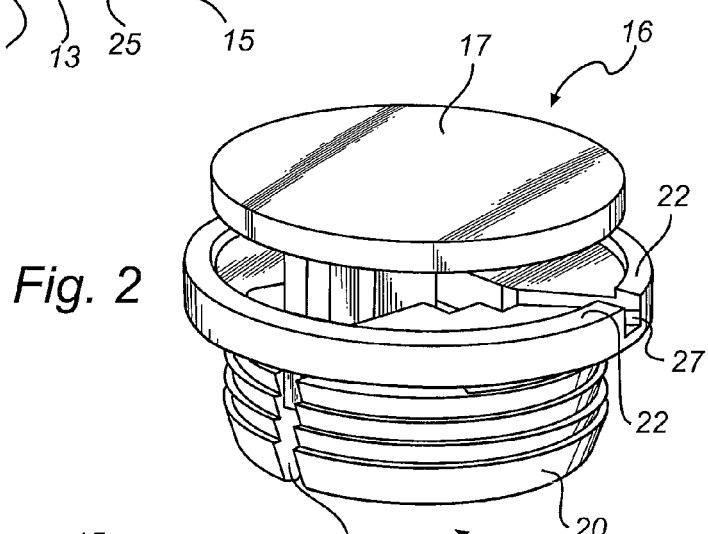
FIG. 2 is a cross-sectional view of the embodiment in FIG. 1 seen in the direction of arrow A in FIG. 1.
Figure 3:
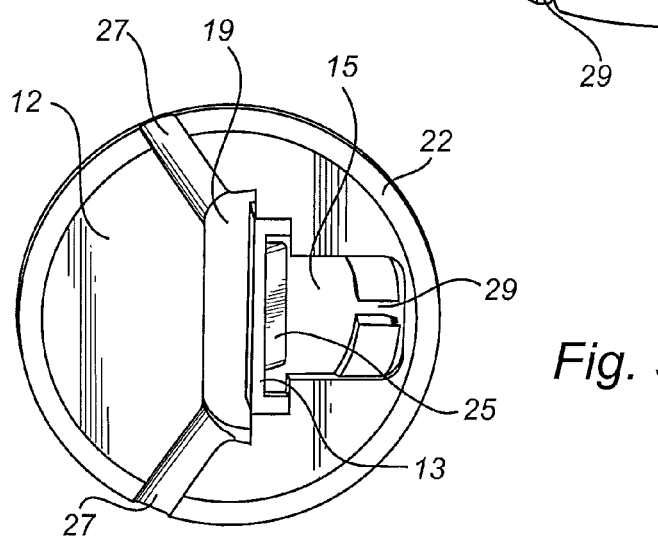
FIG. 3 is a side perspective view of the embodiment illustrated in FIGS. 1 and 2.

Turning now to FIGS. 1-3, an embodiment of the present invention will be discussed. FIG. 1 is an exploded view of an embodiment of the present invention in cross section and FIG. 2 is a cross-sectional view seen in the direction of arrow A in FIG. 1. The securing device 8 includes a circular socket element 10 comprising an upper flange portion 12 and a grommet portion 11. In embodiment of the present invention, the outside of the grommet portion may be provided with circumferential ribs 20 to form a threaded outer surface. The ribs 20 engage the side wall of the burr hole to enhance the security of the engagement of the outer wall of the grommet portion 11 with the burr hole side wall. In this embodiment, the grommet portion 11 is further provided with a slot 29 (see FIG. 2), which in this illustrated embodiment is a split.

A through passage (lead passage) 19 is centrally arranged in the socket element 10 to have a medical lead to pass therethrough. The lead passage 19 is defined by a resilient partition wall 13 connected partly, or wholly, to the inner wall of the grommet portion 11 and a longitudinal partition wall 14 connected to the inner wall of the grommet portion 11. The resilient partition wall 13 delimits an inner compartment 15, where the inner compartment is further delimited by the inner wall of the grommet portion 11.

The securing device 8 further includes a cap element 16 having a circular upper portion 17 being arranged to mate with the socket element 10. To elaborate, the upper portion 17 of the cap element 16 is designed to mate with an upper part of the flange portion 12, which upper part is surrounded by a circumferential ridge 22, so as to seal the securing device when located in the burr hole of the cranium. The circular upper portion 17 will, after being fit into the socket element 10 located in the burr hole, function as a lid of the cranium plug and thus form an outer surface together with the cranium. An inner surface 23 of the cap element 16 is provided with a protruding member 18 arranged to co-operate with the inner compartment 15 when placed into the compartment so as to apply a radial pressure on the resilient partition wall 13 such that a lead (not shown) passing through the lead passage 19 is fixated in the passage 19 by a radial pressing force resulting from the applied radial pressure on the partition wall 13. Thus, the partition wall 13 functions as an intermediary force transmitting means between the protruding member 18 and the lead and thereby tractions or pressure forces in other directions than the radial direction can be substantially eliminated.

The protruding member 18 is in this embodiment shaped as a quadratic element. However, as the skilled person realizes, there are a number of conceivable shapes that also will fulfil the intended purpose of the protruding member 18, for example, a square-like shape or spear-like shape (i.e. a square or quadratic part having a lower edge shaped as a pyramid).

Further, the partition wall 13 is arranged with pressure enhancement means 25 which co-operates with the protruding member 18, when the protruding member is pushed into the compartment 15, to enhance the applied pressure. In this embodiment, the pressure enhancement means 25 is designed as an oblique shoulder 18 arranged on a face of the partition wall 13 facing the compartment 15. Thereby, the protruding member 18 will, when pushed into place, gradually push the resilient partition wall 13 against a lead passing through the lead passage 19 and thus press the lead against the partition wall 14 in a radial direction. Moreover, the protruding member 18 is designed to fit into the slot 29 of the grommet portion 11 so as to, when pushed into the compartment 15 and thus also into the slot 29, apply an expansion force expanding the radius of the grommet portion 11 to more securely fixate the socket element 10, and thus the securing device 8, within the burr hole.

As can be seen in FIGS. 1-3, the upper flange portion 12 and the circumferential ridge 22 are arranged with at least one groove 27 extending from an outer periphery of the flange portion 12 and to the lead passage 19. In this illustrated embodiment, two lead grooves 27 are arranged in the upper flange portion 12 and the circumferential ridge 22. The grooves 27 are designed to accommodate a lead.

As illustrated in FIG. 3, the lead passage 19 has an oblong cross-sectional shape. Thereby, it is possible to eliminate or significantly reduce undesired bending or curvature of the lead since the lead can be fixated anywhere in the lead passage 19. Thereby, it is possible to compensate for a misalignment of the centre of the securing device 8 (seen from the direction of the arrow A) and the lead positioned within the brain of the patient.

Hereinafter, the use of the present invention in a surgical procedure to implant a neurostimulation system for DBS ("Deep Brain Stimulation") will be briefly discussed. The surgical procedure begins with placing a stereotactic headframe around the patient's head to keep the head stationary. The stereotactic frame also helps the surgeon in the placement of the lead used for the stimulation. Thereafter, the surgeon obtains images of the brain using imaging equipment such as, for example, computed tomography (CT) or magnetic resonance imaging (MRI) to map the brain and localize a target site within the brain. In order to provide access to the brain, the surgeon drills a burr hole into the patient's skull. Then, the surgeon inserts a temporary recording stimulation lead into the target site of the brain to test the stimulation, for example, to maximize symptom suppression and minimize side effects before placement of a permanent stimulation electrode lead. When the exact target site of the brain has been determined by the surgeon, the temporary stimulation lead is removed and the surgeon commences the process of inserting the permanent stimulation electrode lead. The stimulation electrode lead passes through the lead passage 19 during the procedure. Using the stereotactic frame and a hydraulic drive, the stimulation electrode lead is inserted through the burr hole together with the socket element 10 in the patient's skull. When it is verified that the electrodes are positioned at the stimulation sites, the lead is placed in one of the grooves 27 and it is ascertained that the socket element 10 is fixated within the burr hole and, then, the cap element 16 is fitted into the socket element 10 to secure the lead in the lead passage 19 and the socket element 10 within the burr hole. Once the lead is positioned and tested to determine that the results of stimulation are satisfactory, it is critical that it is not moved. A movement as little as one millimeter of electrode displacement may cause unsatisfactory results or even injury to the brain. Traction on the portion of the lead positioned outside the cranium may cause movement on the portion of the lead positioned within the brain. As understood, it is crucial to achieve a firm and reliable anchoring of the lead in the burr hole. The present invention provides for a reliable anchoring of the lead within the burr hole due to the traction free fixation process of the lead.

Figure 4:
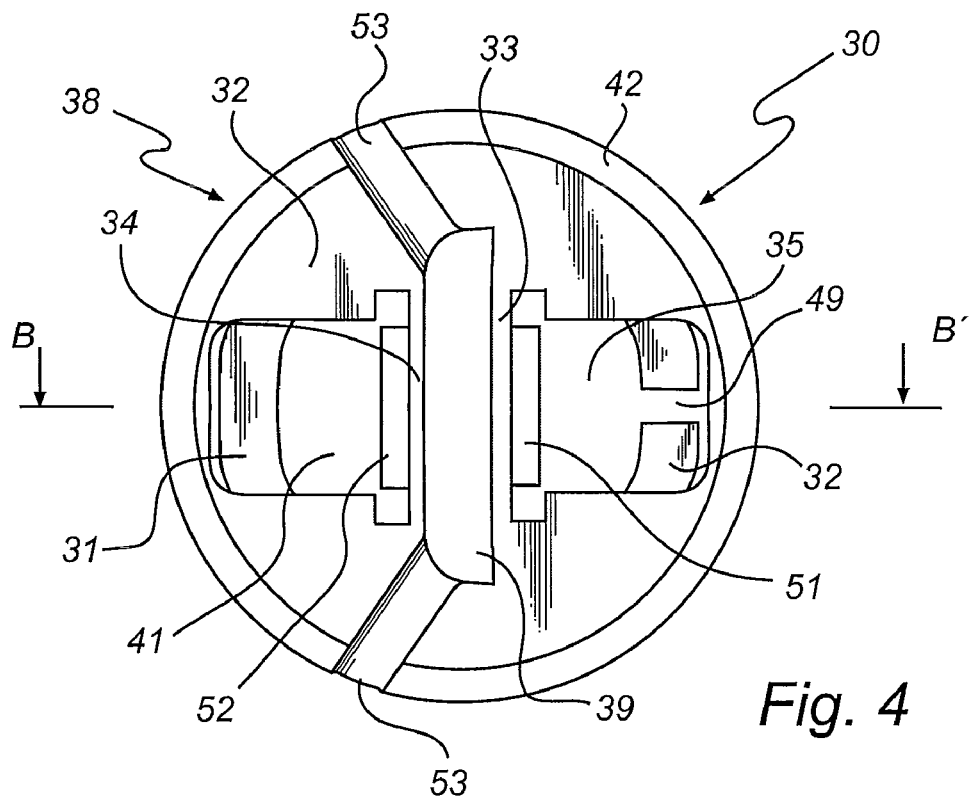
FIG. 4 an exploded view of an embodiment of the present invention in cross section.
Figure 5:
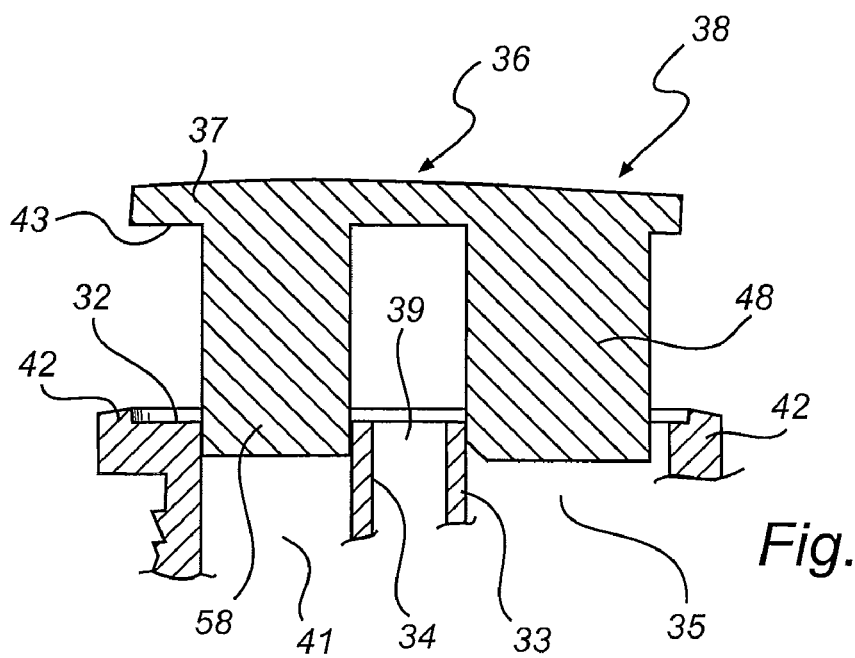
FIG. 5 is a cross-sectional view of the embodiment in FIG. 4 along the direction B-B'.

With reference now to FIGS. 4 and 5, a further embodiment of the present invention will be discussed. The use and function of this embodiment is essentially similar to the embodiment described above. FIG. 4 illustrates a socket element of a further embodiment of the present invention in a view corresponding to that one illustrating the socket element in FIG. 3. Further, FIG. 5 is a cross-sectional view of the cap element adapted to mate with the socket element shown in FIG. 4. The securing device 38 includes a circular socket element 30 comprising an upper flange portion 32 and a grommet portion 31. In an embodiment of the present invention, the outside of the grommet portion may be provided with circumferential ribs 20 to form a threaded outer surface. The circumferential ribs 20 engage the side wall of the burr hole to enhance the security of the engagement of the outer wall of the grommet portion 31 with the burr hole side wall. In this embodiment, the grommet portion 31 is further provided with a split 49.

A through passage (lead passage) 39 is centrally arranged in the socket element 30 to have a medical lead to pass therethrough. The lead passage 39 is defined by a first resilient partition wall 33 connected partly, or wholly, to the inner wall of the grommet portion 31 and a second resilient partition wall 34 connected partly, or wholly, to the inner wall of the grommet portion 31. The first resilient partition wall 33 delimits a first inner compartment 35, which first inner compartment 35 is further delimited by the inner wall of the grommet portion 31. Further, the second resilient partition wall 34 delimits a second inner compartment 41, which second inner compartment 41 is further delimited by the inner wall of the grommet portion 31.

The securing device 38 further includes a cap element 36 (see FIG. 5) having a circular upper portion 37 being arranged to mate with the socket element 30. To elaborate, the upper portion 37 of the cap element 36 is designed to mate with an upper part of the flange portion, which upper part is surrounded by a circumferential ridge 42, so as to seal the securing device when located in the burr hole of the cranium. The circular upper portion 37 will, after being fit into the socket element 30 located in the burr hole, function as a lid of the cranium plug and thus form an outer surface together with the cranium. An inner surface 43 of the cap element 36 is provided with a first protruding member 48 arranged to co-operate with the first inner compartment 35 when placed into the compartment so as to apply a radial pressure on the first resilient partition wall 33 and a second protruding member 58 arranged to co-operate with the second inner compartment 41 when placed into the compartment so as to apply a radial pressure on the second resilient partition wall 34. Thereby, a lead (not shown) passing through the lead passage 39 will be fixated in the passage 39 by radial pressing forces resulting from the applied radial pressure on the first and second partition walls 33 and 34, respectively. Thus, the partition walls 33, 34, respectively, function as intermediary force transmitting means between the protruding members 48, 58, respectively, and the lead so as tractions or pressure forces in other directions than the radial direction can be substantially eliminated.

The protruding members 48, 58, respectively, are in this embodiment shaped as quadratic elements. Further, the first and second partition walls 33 and 34, respectively, are arranged with pressure enhancement means 51 and 52 which co-operate with the protruding members 48 and 58, respectively, when respective protruding member 48 and 58 is pushed into respective compartment 35 and 41, respectively, to enhance the applied pressure. In this embodiment, the pressure enhancement means 51 and 52 are designed as oblique shoulders arranged on a face of the respective partition wall 33 and 34 facing the respective compartment 35 and 41. Thereby, the protruding members 48 and 58 will, when pushed into place, gradually push the respective resilient partition wall 33 and 34 against a lead passing through the lead passage 39 towards each other in a radial direction and thus clamp the lead between each other. Moreover, the protruding member 48 is designed to fit into the split 49 of the grommet portion 31 so as to, when pushed into the compartment 35 and thus also the split 49, apply an expansion force expanding the radius of the grommet portion 31 to more securely fixate the socket element 30, and thus the securing device 38, within the burr hole.

As can be seen in FIG. 4, the upper flange portion 32 and the circumferential ridge 42 is arranged with at least one groove 53 extending from an outer periphery of the flange portion 32 and to the lead passage 39. In this illustrated embodiment, two lead grooves 53 are arranged in the upper flange portion 32 and the circumferential ridge 42.

As illustrated in FIG. 4, the lead passage 39 has an oblong cross-sectional shape. Thereby, it is possible to eliminate or significantly reduce undesired bending or curvature of the lead since the lead can be fixated anywhere in the lead passage 39. Thereby, it is possible to compensate for a misalignment of the centre of the securing device 38 (seen from the direction of the arrow A) and the lead positioned within the brain of the patient.

According to embodiments of the present invention, the socket member can be made of polymer like polysylfone and the cap plate can be made of elastic material like silicone.

In a further embodiment of the present invention, the cap element 16 is bendable or foldable. For example, the circular element 17 may be provided with hinge means that entails that the cap element 16 can be inserted into the socket element 10 before the lead has been finally positioned. When the lead has been positioned, the foldable part of the cap element 16 is folded down and the socket element 10 is sealed and secured into the burr hole and the lead is secured in the lead passage 19. In one embodiment, the foldable part is provided with the protruding member 18.

Even though the present invention has been described above using exemplifying embodiments thereof, alterations, modifications, and combinations thereof, as understood by those skilled in the art, may be made without departing from the scope of the invention as defined in the accompanying claims.

The invention claimed is:

1. A device for securing a medical lead within a cranial hole, comprising:
   a socket element adapted to be secured within a burr hole of the skull of a patient, said socket element having a lead passage arranged to have the medical lead pass therethrough, said lead passage delimited by passage walls including at least one resilient partition wall extending from an inner wall of said socket element, and said socket element having at least one inner compartment delimited by said at least one resilient partition wall;
   a cap element having an upper portion arranged to mate with said socket element, said upper portion having at least one protruding member arranged to co-operate with said at least one inner compartment when placed into said at least one inner compartment so as to apply a radial pressure on said at least one resilient partition wall such that the medical lead passing through said lead passage is fixated in said lead passage by a resulting radial pressing force, wherein said resilient partition wall is located between said lead passage and said inner compartment, and when said protruding member is placed into said inner compartment, a radial inward pressure is exerted on said resilient partition wall.

2. The device according to claim 1, wherein said at least one protruding member is arranged to engage with a slot in an outer wall of said socket element such that said socket element is secured in said burr hole by an expansion force.

3. The device according to claim 1, wherein said lead passage is delimited by a non-resilient longitudinal passage wall and said resilient partition wall, wherein said medical lead, in a fixated state, is fixated between said resilient partition wall and said non-resilient passage wall by means of the radial pressure force applied by said protruding member.

4. The device according to claim 1, wherein an upper surface of said socket element facing said cap element when said cap element is fitted in said socket element is arranged with at least one groove from an outer periphery of said socket element to said lead passage, wherein said medical lead can be fitted into said at least one groove.

5. The device according to claim 1, wherein said resilient partition wall includes a pressure enhancement structure configured to co-operate with said protruding element so as to enhance said radial pressure.

6. The device according to claim 1, wherein said resilient partition wall includes an inclined shoulder arranged on a side of the resilient partition wall facing the inner compartment, said inclined shoulder being arranged to co-operate with protruding element so as to enhance said radial pressure.

7. The device according to claim 2, wherein said slot is a throughgoing slit.

8. The device according to claim 1, wherein said upper portion of said cap element is arranged to be partly foldable.

9. The device according to claim 2, wherein said lead passage is delimited by a non-resilient longitudinal passage wall and said resilient partition wall, wherein said medical lead, in a fixated state, is fixated between said resilient partition wall and said non-resilient passage wall by means of the radial pressure force applied by said protruding member.

10. The device according to claim 2, wherein an upper surface of said socket element facing said cap element when said cap element is fitted in said socket element is arranged with at least one groove from an outer periphery of said socket element to said lead passage, wherein said medical lead can be fitted into said at least one groove.

11. The device according to claim 3, wherein an upper surface of said socket element facing said cap element when said cap element is fitted in said socket element is arranged with at least one groove from an outer periphery of said socket element to said lead passage, wherein said medical lead can be fitted into said at least one groove.

12. The device according to claim 1, further including:
a first inner compartment delimited by a first resilient partition wall and an inner wall of a grommet portion of said socket element;
a second inner compartment delimited by a second resilient partition wall and said inner wall of said grommet portion of said socket element;
a first protruding member arranged to co-operate with said first inner compartment when placed into said compartment so as to apply a radial pressure on said first resilient partition wall;
a second protruding member arranged to co-operate with said first inner compartment when placed into said compartment so as to apply a radial pressure on said second resilient partition wall; and
wherein a lead passing through said passage is fixated in said through lead passage by resulting radial pressing forces.

13. The device according to claim 12, wherein said first protruding member is arranged to engage with a slot in said grommet portion such that said socket element is secured in said burr hole by an expansion force.

14. The device according to claim 12, wherein said through lead passage is delimited by said first and said second resilient partition walls, wherein said lead, in a fixated state, is fixated between said first and second resilient partition walls by means of the radial pressure force applied by said first and second protruding members.

15. The device according to claim 12, wherein
said first resilient partition wall is arranged with pressure enhancement means for co-operation with said first protruding member to enhance an applied radial pressure; and wherein
said second resilient partition wall is arranged with pressure enhancement means for co-operation with said second protruding member to enhance an applied radial pressure.

16. The device according to claim 15, wherein said pressure enhancement means is designed as oblique shoulders arranged on a face of respective first and second partition wall facing the first and second inner compartment, respectively.

17. The device according to claim 12, wherein an upper surface of said circular socket element facing said cap element when said cap element is fitted in said socket element is arranged with at least one groove from an outer periphery of said socket element to said lead passage, wherein said lead can be fitted into said groove.

18. The device according to claim 13, wherein said slot is a through going slit.

19. The device according to claim 13, wherein said lead passage is delimited by said first and said second resilient partition walls, wherein said lead, in a fixated state, is fixated between said first and second resilient partition walls by means of the radial pressure force applied by said first and second protruding members.

20. The device according to claim 13, wherein an upper surface of said circular socket element facing said cap element when said cap element is fitted in said socket element is arranged with at least one groove from an outer periphery of said socket element to said lead passage, wherein said lead can be fitted into said groove.

21. The device according to claim 20, wherein an upper surface of said circular socket element facing said cap element when said cap element is fitted in said socket element is arranged with at least one groove from an outer periphery of said socket element to said lead passage, wherein said lead can be fitted into said groove.

* * * * *